(12) United States Patent
Wells

(10) Patent No.: US 6,372,440 B2
(45) Date of Patent: Apr. 16, 2002

(54) METHOD FOR DETECTING DEFICIENT CELLULAR MEMBRANE TIGHTLY BOUND MAGNESIUM FOR DISEASE DIAGNOSES

(75) Inventor: Ibert C. Wells, Omaha, NE (US)

(73) Assignee: Magnesium Diagnostics, Inc., Omaha, NE (US)

( * ) Notice: Subject to any disclaimer, the term of this patent is extended or adjusted under 35 U.S.C. 154(b) by 0 days.

(21) Appl. No.: 09/265,690

(22) Filed: Mar. 10, 1999

(51) Int. Cl.$^7$ .......................... G01N 33/53; A01N 25/00
(52) U.S. Cl. .......................... 435/7.1; 435/7.72; 435/7.9; 435/7.93; 435/7.94; 435/7.95; 514/866; 540/597; 540/598
(58) Field of Search ................................. 435/7.1, 7.72, 435/7.9, 7.93, 7.94, 7.95; 514/866; 540/597, 598

(56) References Cited

U.S. PATENT DOCUMENTS

| | | |
|---|---|---|
| 5,268,359 A | 12/1993 | Harmar et al. |
| 5,491,140 A | 2/1996 | Bruns, Jr. et al. |
| 5,492,927 A | 2/1996 | Gitter et al. |
| 5,525,624 A | 6/1996 | Gitter et al. |
| 5,563,133 A | 10/1996 | Hipskind |
| 5,565,568 A | 10/1996 | Cho et al. |
| 5,594,022 A | 1/1997 | Horwell et al. |
| 5,607,947 A | 3/1997 | Hipskind |
| 5,610,176 A | 3/1997 | Horwell et al. |
| 5,616,562 A | 4/1997 | Murphy et al. |
| 5,670,499 A | 9/1997 | Cho et al. |
| 5,684,033 A | 11/1997 | Cho et al. |
| 5,698,710 A | 12/1997 | Sisto et al. |

OTHER PUBLICATIONS

Theodorsson–Norheim et al; Neuropeptide K: A Major Tachykinin I Plasma And Tumor Tissues From Carcinoid Patients. Biochemical And Biophysical Research Communications; 131, 77–83, 1985.*

Frickey et al; Preparation And Characterization Of Monoclonal Antibodies To Substance P; Hybridoma 10; 685–693, 1991.*

Bioorganic & Medicinal Chemistry, vol. 4 No. 10, pp. 1573–1576, 1996 entitled: Use of the Chemical Structure of Peptides as the Starting Point to Design Nonpeptide Agonists and Antagonists at Peptide Receptors: Examples with Cholecystokinin and Tachykinins by David C. Horwell.

Edvinsson, L., et al., "Reducted levels of calcitonin gene–related peptide (CGRP) but not substance P during and after treatment of severe hypertension in man," *J. Human Hypertension*, 1989, 3:267–270.

Faulhaber, H.D., et al., "Substance P in Human Essential Hypertension," *J. Cardiovasc. Pharmacol.*, 1987, 10(Suppl. 12):S172–S176.

Mattingly, M.T., et al., "Decreased Cell Membrane Magnesium in Some Essential Hypertension Patients," Clin. and Exper. Hyper.—Theory and Practice, 1991, A13(1):65–82 (author's reprint enclosed–total of 20 pages).

Meyer, P., and Marche, P., "Cell Membrane in Hypertension," *The American Journal of Medical Sciences*, Apr. 1988, 295(4):396–399.

Mori, K., et al., "Decreases in Substance P and Vasoactive Intestinal Peptide Concentrations in Plasma of Stroke–Prone Spontaneously Hypertensive Rats," *Jpn. Heart J.*, Nov. 1993, 34(6):785–794.

Resnick, L.M., et al., "Intracellular free magnesium in erythrocytes of essential hypertension: Relation to blood pressure and serum divalent cations," *Proc. Natl. Acad. Sci. USA*, Oct. 1984, 81:6511–6515.

Sanfilippo, J.S., et al., "Amniotic Fluid Levels of Substance P," *The Journal of Reproductive Medicine*, Aug. 1992, 37(8):733–736.

Takano, Y., et al., "Substance P immunoreactivity released from rat spinal cord after kainic acid excitation of the ventral medulla oblongata: a correlation with increases in blood pressure," *Brain Research*, 1984, 291:168–172.

Wells, I.C., and Agrawal, D.K., "Abnormal magnesium metabolism in two rat models of genetic hypertension," *Can. J. Physiol. Pharmacol.*, 1992, 70:1225–1229.

* cited by examiner

Primary Examiner—Lynette F. Smith
Assistant Examiner—Padma Baskar
(74) Attorney, Agent, or Firm—Rothwell, Figg, Ernst & Manbeck

(57) ABSTRACT

This invention relates to methods for detecting the deficiency of magnesium tightly bound to cellular membranes, i.e. magnesium binding defect, which deficiency is associated with certain abnormal physiological states e.g., salt-sensitive essential hypertension or Type 2 diabetes mellitus.

7 Claims, No Drawings

SEQUENCE LISTING

```
<160> NUMBER OF SEQ ID NOS: 4

<210> SEQ ID NO 1
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: AMIDATION

<400> SEQUENCE: 1

Phe Phe Gly Leu Met
1               5

<210> SEQ ID NO 2
<211> LENGTH: 4
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: AMIDATION

<400> SEQUENCE: 2

Phe Gly Leu Met
1

<210> SEQ ID NO 3
<211> LENGTH: 11
<212> TYPE: PRT
<213> ORGANISM: Homo sapiens
<220> FEATURE:
```

```
<221> NAME/KEY: MOD_RES
<222> LOCATION: (11)..(11)
<223> OTHER INFORMATION: AMIDATION

<400> SEQUENCE: 3

Arg Pro Lys Pro Gln Gln Phe Phe Gly Leu Met
1               5                   10

<210> SEQ ID NO 4
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: AMIDATION
<221> NAME/KEY: VARIANT
<222> LOCATION: (2)..(2)
<223> OTHER INFORMATION: "X" may be either Phe or Val.

<400> SEQUENCE: 4

Phe Xaa Gly Leu Met
1               5
```

METHOD FOR DETECTING DEFICIENT CELLULAR MEMBRANE TIGHTLY BOUND MAGNESIUM FOR DISEASE DIAGNOSES

BACKGROUND OF THE INVENTION

1. Field of Invention

This invention relates to methods and diagnostic kits for detecting the cellular membrane magnesium binding defect, which deficiency is critically associated with certain abnormal physiological states, e.g. sodium-sensitive essential hypertension and type 2 insulin-resistant diabetes mellitus.

2. Description of the Prior Art

Elevated arterial pressure, namely hypertension, is probably among the most important public health problems in developed countries. It is of common occurrence, asymptomatic, readily detectable, and often leads to lethal complications if not treated. Although there are exceptions, most untreated adults with hypertension will continue to experience further increases in their arterial pressure over time. Reports based on actuarial data and clinical experience, estimate that untreated hypertension shortens life by 10 to 20 years. This lower life expectancy is believed to be due to an acceleration of the atherosclerotic process, with the rate of acceleration related in part to the severity of the hypertension. Even individuals with relatively mild disease—those individuals without evidence of end-organ damage—if left untreated for 7 to 10 years have a high risk of developing significant complications, and more than 50 percent of them will ultimately experience end-organ damage related to hypertension. End organ damage can include cardiomegaly, congestive heart failure, retinopathy, a cerebrovascular accident, and/or renal insufficiency. Thus, even in its mild forms, hypertension can be a lethal disease, if left untreated.

Although awareness of the problems associated with elevated arterial pressure has increased, in 90 to 95 percent of the 60 million, minimally estimated, existing cases in the United States, the cause of the disease, and thus potentially its prevention and cure, is still largely unknown. These individuals have only generalized or functional abnormalities associated with their hypertension and are often diagnosed as having primary, idiopathic or essential hypertension. Several abnormalities have been identified in patients with essential hypertension (see e.g., Meyer P and Marche P, Am. J. Med. Sci. 295: 396–399 (1988)), often with claims, later contested or unsubstantiated, of the abnormalities being primarily responsible for the hypertension. This situation has been attributed generally to the likely possibility that essential hypertension has more than one cause, each of which may be a set of genetically determined, contributory abnormalities, which in turn interact with environmental factors.

The most widely recognized of these possible causes of essential hypertension is sodium, i.e. sodium ion (Na+) sensitivity, also commonly referred to as salt (NaCl)-sensitivity. In such patients hypertension is exacerbated by a high dietary salt intake and diminished by dietary salt restriction. It has been assumed that this abnormality reflects cellular membrane defect, and that this defect occurs in many, perhaps all, cells of the body, particularly the vascular smooth muscle cells. Based on studies using erythrocytes, this defect has been estimated to be present in 35 to 50 percent of the essential hypertension population.

However, Applicant discovered, as disclosed below, the actual complex mechanism underlying sodium-sensitive hypertension, which discovery has yielded a new diagnostic methodology to detect this disease at its early stages.

Type 2 diabetes mellitus is the most common form of diabetes mellitus, comprising 85–90% of the diabetic population and taking heterogeneous forms. Overt diabetes characteristically appears after the age of 40, has a high rate of genetic penetrance unrelated to HLA genes, and is associated with obesity. A strong hereditary component is evident. For example, concordance rates in identical twins is nearly 100 percent.

Among American whites the estimated incidence of Type 2 diabetes mellitus in 1976 was between 1 and 2 percent, but the prevalence has risen as the population has aged and become more obese. More than 10 percent of the older population now suffers from the disease. According to the 1990–1992 National Health Interview Survey, about 625,000 cases of diabetes are diagnosed in the United States each year—more than 6 times the 1935–36 rate.

Many consider insulin resistance to be the primary cause of Type 2 diabetes mellitus. This pathological state and the consequent hyper-insulinemia develop years before insulin secretion diminishes and overt diabetes mellitus is present. About 20 percent of the white population of the United States has impaired glucose tolerance, i.e. hyperglycemia—the virtually universally accepted sign of the presence of diabetes mellitus.

Patients affected with overt Type 2 diabetes mellitus retain some endogenous insulin-secreting capacity, but insulin levels in plasma are low relative to the magnitude of insulin resistance and ambient plasma glucose levels. Such patients do not depend on insulin for immediate survival and rarely develop diabetic ketosis.

The clinical presentation of Type 2 diabetes mellitus is insidious. The classical symptoms of diabetes may be mild and tolerated for a long time before the patient seeks medical attention. Moreover, if hyperglycemia is asymptomatic, the disease becomes clinically evident only after complications develop. Such complications include atherosclerosis, the risk for which is greatest in poorly controlled patients. Other sequela of diabetes mellitus are myocardial infarction, stroke, peripheral vascular disease and lower extremity gangrene, neuropathy, nephropathy, diabetic foot syndrome, cardiomyopathy and dermopathy.

Little is known about the specific genetic abnormalities associated with most forms of Type 2 diabetes mellitus. However, applicant has observed the highly frequent occurrence of the magnesium binding defect in the erythrocyte membranes of mildly affected Type 2 diabetics.

Others have found insulin resistance to be caused by what was ostensibly the magnesium binding defect. (See Mattingly MT, Brzezinske WA, Wells IC, Clin. Exper. Hypertension—Theory and Practice A13: 65–82 (1991).

These observations strongly support the concept that the magnesium binding defect, which is genetic, is the cause of insulin resistance. Therefore, the detection of the presence of this defect in an individual who is asymptomatic would indicate the presence of Type 2 diabetes mellitus in its earliest stage so that management of the disease could begin at the earliest possible time.

SUMMARY OF THE INVENTION

This invention involves methods for the detection in humans of physiological disorders, such as sodium-sensitive, essential hypertension and adult onset, Type 2, insulin resistant diabetes mellitus, for which the subnormal binding of magnesium to cellular membranes of the somatic cells is a contributory, critical cause. These methods comprise the quantification of the concentrations, in blood plasma from the above individuals, of the polypeptide degradation products derived from the amidated C-terminal region of the tachykinins such as Substance P. These degradation products are embodied in the amino acid sequence of the pentapeptide which characterizes the amidated, C-terminal amino acid sequences of all of the tachykinins, of mammalian origin, i.e. Phe-X(Phe, Val)-Gly-Leu-Met-NH$_2$.

DETAILED DESCRIPTION OF THE PREFERRED EMBODIMENTS

Applicant quantified the magnesium contents of the several anatomical compartments of whole blood from some essential hypertension patients and normotensive control subjects and discovered several differences. The most noteworthy difference was the decreased levels of magnesium firmly bound to the erythrocyte membranes of the hypertensive patients. The magnitude of this previously unknown defect correlated positively with the magnitude of the decreased concentration of intracellular magnesium which in turn correlated positively with the average blood pressures of the patients. Further, another novel observation was that this magnesium binding defect was corrected by incubating the erythrocytes from the hypertensive patients with blood plasma from the control subjects (Mattingly MT, Brezezinski WA, Wells IC, Clin. Exper. Hypertension-Theory and Practice A13: 65–82 (1991)).

This investigation was extended to include two strains of genetic, sodium-sensitive, hypertensive rats, i.e. the SHR and SS/Jr rats, and their respective normotensive controls, i.e. the WKY and SR/Jr rats (Wells IC and Agrawal DK, Can. J. Physiol. Pharmacol. 70: 1225–1229 (1992)). The magnesium binding defect was also observed to occur in these two strains of hypertensive rats as well as in the SR/Jr normotensive strain. It was concluded from these observations that the magnesium binding defect could only be a contributory, though perhaps a critical, cause of hypertension generation. Other investigators have collected evidence to indicate that in these two hypertensive rat strains the enzyme systems required for the extrusion of excess sodium ion from the cells, i.e. the Na$^+$, K$^+$-ATPase and/or the Na$^+$, K$^+$-cotransport enzyme, are defective and that the passive permeability of the cell membranes for sodium ion of the SHR rat is greater than that of the control WKY rat.

Accordingly, Applicant made several conclusions about the mechanisms of hypertension generation in the SHR and SS/Jr rats (both of which exhibit sodium-sensitive hypertension). First, the magnesium binding defect in the cellular membrane of the vascular smooth muscle cell, for example, and perhaps those of all somatic cells, permits per unit of time more than the normal amounts of sodium ion to enter passively into the cell even though the extracellular concentration of this ion is normal. Second, because the enzyme systems which remove excess sodium ion from the cell are defective, the intracellular sodium ion concentration increases to above normal levels. Third, because the extracellular sodium ion concentration tends to remain greater than the intracellular concentration, the sodium-calcium exchange enzyme within the cell membrane begins to export sodium ion from the cell and to import calcium ion. Fourth, the resulting increased intracellular calcium ion concentration stimulates the smooth muscle to contract. When the vascular smooth muscle contracts, the lumens of the arterioles in the peripheral circulation decrease in diameter thereby increasing the resistance to blood flow. Finally to overcome this increased resistance to blood flow, the heart must contract more strongly and this increased force is reflected as increased blood pressure.

As indicated above, the normotensive SR/Jr rat also has the magnesium binding defect. However, this rat is normotensive and can tolerate greatly elevated levels of dietary NaCl ostensibly because its sodium ion extrusion enzymes adequately prevent an increase in the intracellular concentration of this ion.

The results of further experimentation employing the two sodium-sensitive hypertensive rat strains are as follows. The total intracellular concentrations of sodium, potassium and calcium in the sodium-sensitive, hypertensive SHR and SS/Jr rats, as compared to those of the normotensive WKY and SR/Jr rats, are entirely consistent with the above postulated mechanism, i.e. elevated concentrations of sodium and calcium, decreased concentration of potassium. The substances in normal human and rat plasmas that correct the magnesium binding defect in erythrocyte membranes were identified as the pentapeptide Phe-Phe-Gly-Leu-Met-NH$_2$ (SEQ ID NO:1) and the tetrapeptide Phe-Gly-Leu-Met-NH$_2$ (SEQ ID NO:2) which occur at the C-terminal end of the tachykinin Substance P whose amino acid sequence is Arg-Pro-Lys-Pro-Gln-Gln-Phe-Phe-Gly-Leu-Met-NH$_2$ (SEQ ID NO:3).

Evidence was obtained to indicate that the generalized C-terminal sequence of the tachykinins Phe-X(Phe, Val)-Gly-Leu-Met-NH$_2$ (SEQ ID NO:4) embodies the substances in normal plasma which prevent the magnesium binding defect in cellular membranes. This defect plays a critical role in the genesis of sodium-sensitive hypertension and Type 2 diabetes mellitus. Further, the intravenous administration of the pentapeptide of SEQ ID NO: 1 to the sodium sensitive SS/Jr rat not only corrected the magnesium binding defect in its erythrocytes but also reduced its systolic blood pressure from an elevated value of 210 mm Hg to a normal value<than 160 mm Hg.

It is apparent that an essential hypertensive person in whom the magnesium binding defect exists is, to a very high degree of probability, a sodium-sensitive hypertensive and that the restriction of the dietary intake of sodium chloride (and other sources of sodium ion) by this individual would be therapeutically beneficial. Contrariwise, an essential hypertensive person without the magnesium binding defect is in all probability a sodium-insensitive hypertensive. Not only would such a person suffer needlessly if restricted to the minimum dietary sodium chloride intake consistent with a healthy existence but there is evidence to indicate that such a diet would be harmful for certain ones of these essential hypertensive persons.

It is further apparent that a method that would permit the rapid and accurate determination of the blood plasma levels of the polypeptides which have the amino acid sequences corresponding to those of SEQ ID NO:1, SEQ ID NO:2 or SEQ ID NO:4 all of which are equally active in preventing or correcting the magnesium binding defect, would be of value to a clinician for the diagnosis and treatment of essential hypertension. It is realistic to expect that if the blood plasma levels of these compounds are subnormal in an essential hypertensive patient, the magnesium binding defect is present and that the hypertension can be classified as sodium-sensitive and can therefore be treated appropriately. On the other hand, if the concentrations of these substances are at least normal, then the magnesium binding defect is not present and the hypertension belongs to the salt-insensitive classification. Also, applicant has observed the highly frequent occurrence of the magnesium binding defect in the erythrocyte membranes of mildly affected Type 2 diabetics, as discussed above, and analogous considerations would apply for the diagnosis of this disease.

A most preferred embodiment of this invention employs irumunochemical procedures (i.e., "binding assays") to detect the occurrence of the magnesium binding defect. This invention involves binding assays wherein a binding pair member having affinity to one or more of the polypeptides listed above is employed to detect the amount(s), presence or absence of the polypeptide(s) in question in blood plasma. A preferred binding pair member is an antibody. Both direct and indirect procedures are used with known or constant, but unknown, concentrations of polypeptide (analyte) and antibody to determine the quantitative relationship between the two substances. This calibration procedure requires that either the analyte or antibody be labeled, either before or subsequent to binding, with an easily and accurately quantifiable material so that from the quantity of label present after the binding procedure and the previously determined binding relationship, the amount of analyte initially subjected to the binding reaction can be determined with acceptable accuracy. This methodology is widely known and extensively utilized because the extreme sensitivity possible with this method allows the quantification of physiological important, low molecular weight analytes such as steroid hormones, e.g. progesterone, in biological fluids, e.g. blood plasma, at concentrations in the picogram, i.e. $10^{-12}$ grams, per mL range. The construction and utilization of various such assay systems can be accomplished by one skilled in the art. Examples of such systems are described and discussed in detail in An Introduction to Radioimmunoassay and Related Techniques, fourth edition, by T. Chard: 1990; Elsiever Science Publishing Co., Inc.; New York which reference is incorporated herein.

For the purpose of illustration, the construction of a suitable assay system for the determination of the concentrations of the polypeptides of interest in blood plasma is as follows. Since each of the polypeptides above has only one, and the same, immunological combining site, namely the pentapeptide of SEQ ID NO:1, suitable modifications of it will be used for labeling with a label such as the radioisotope, iodine-125, and for the raising of the necessary antibody. SEQ ID NO:1, its analog in which one of the phenylalanine (Phe) residues is replaced with a tyrosine (Tyr) residue, and its deamidated product are available from commercial sources, e.g. (Sigma Chemical Co., St. Louis, Mo.). The Tyr analog is labeled with iodine-125 by procedures described in the above reference and is used as the "trace analyte". The deamidated peptide is conjugated with a carrier protein, as described below for use in the production in an animal of a polyclonal antibody having a high titer against the peptide.

Briefly, a polyclonal antibody is prepared by immunizing an animal with an immunogenic protein or polypeptide and collecting antisera from that immunized animal. A wide range of animal species is used for the production of antisera, and the choice is based on the phylogenetic relationship to the antigen. Typically the animal used for production of antisera is a rabbit, a guinea pig, a chicken, a goat, or a sheep. Because of the relatively large blood volumes of sheep and goats, these animals are preferred choices for production of large amounts of polyclonal antibodies.

As is well known in the art, antigenic substances may vary in their abilities to generate an immune response. It is necessary in this case, therefore, to boost the host immune system by coupling such weak immunogens (e.g., a peptide or polypeptide) to a carrier, which is recommended in the present case. Examples of common carriers are keyhole limpet hemocyanin ("KLH", which is preferred in this case) and bovine serum albumin (BSA). Means for conjugating a polypeptide to a carrier protein are well known in the art and include the use of MBS (m-malecimidobenzoyl-N-hydroxysuccimide ester), EDAC (1-ethyl-3-(3-dimethylaminopropyl) carbodiimide hydrochloride), and bisdiazotized benzidine.

The conjugation and antibody production services are also available commercially (e.g., from Rockland, Immunochemicals for Research, Gilbertsville, PA). The pentapeptide SEQ ID NO:1 is used as the analyte standard.

As is also well known in the art, the immunogenicity of a particular immunogen can be enhanced by the use of non-specific stimulators of the immune response, known as adjuvants. Cytokines, toxins or synthetic compositions may also be used as adjuvants. The most commonly used adjuvants include complete Freund's adjuvant (a non-specific stimulator of the immune response containing killed *Mycobacterium tuberculosis*) and incomplete Freund's adjuvant which does not contain the bacteria.

Milligram quantities of antigen (immunogen) are preferred although the amount of antigen administered to produce polyclonal antibodies varies with the nature and composition of the immunogen as well as with the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various times following inoculation.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate monoclonal antibodies (MAbs).

For production of rabbit polyclonal antibodies, the animal can be bled through an ear vein or alternatively by cardiac puncture. The removed blood is allowed to clot and then centrifuged to separate serum components from whole cells and blood clots. Sterility is maintained throughout this preparation. The serum may be used as such for various applications or else the desired antibody fraction may be isolated and purified by well-known methods, such as affinity chromatography using another antibody, a peptide bound to a solid matrix, or by using, e.g., protein A or protein G chromatography.

Instead of using polyclonal antibodies, monoclonal antibodies (MAbs) can be used in the practice of this invention. MAbs may be readily prepared through use of well-known techniques, such as those exemplified in U.S. Pat. No. 4,196,265, incorporated herein by reference. Typically, this technique involves immunizing a suitable animal with a selected immunogen, e.g., a purified or partially purified protein, polypeptide, peptide or domain. The immunizing substance is administered in a manner effective to stimulate antibody producing cells.

The methods for generating monoclonal antibodies (MAbs) generally begin along the same lines as those for preparing polyclonal antibodies. Rodents such as mice and rats are preferred animals; however, the use of rabbit, sheep, or frog cells is also possible. The use of rats may provide certain advantages (Goding, In: *Monoclonal Antibodies: Principles and Practice*, 2d ed., 1986, pp. 60–61), but mice are preferred, with the BALB/c mouse being most preferred as it is routinely used and generally gives a higher percentage of stable fusions.

The animals are injected with antigen, generally as described above. The antigen may be coupled to carrier molecules such as keyhole limpet hemocyanin if necessary. The antigen is typically mixed with adjuvant, such as Freund's complete or incomplete adjuvant. Booster injections with the same antigen are made at approximately two-week intervals.

Following immunization, somatic cells with the potential for producing antibodies, specifically B lymphocytes (B cells), are selected for use in the MAb generating protocol. Antibody-producing B cells are usually obtained by disbursement of the spleen, but tonsil, lymph nodes, or peripheral blood may also be used. Spleen cells are preferred because they are a rich source of antibody-producing cells that are in the dividing, plasmablast stage.

The antibody-producing B lymphocytes from the immunized animal are then fused with cells of an immortal myeloma cell line, generally one from the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). Any one of a number of myeloma cells may be used, as is known to those of skill in the art (Goding, pp. 65–66, 1986).

Methods for generating hybrids of antibody-producing spleen or lymph node cells and myeloma cells usually comprise mixing somatic cells with myeloma cells in about a 2:1 proportion in the presence of an agent or agents (chemical or electrical) that promote the fusion of cell membranes. The original fusion method using Sendai virus has largely been replaced by those using polyethylene glycol (PEG), such as 37% (v/v) PEG, as has been described in the art. The use of electrically induced fusion methods is also appropriate.

Fusion procedures usually produce viable hybrids at low frequencies. However, this does not pose a problem, as the viable, fused hybrids are differentiated from the parental, unfused cells (particularly the unfused myeloma cells that would normally continue to divide indefinitely) by culturing in a selective growth medium. The selective medium is generally one that contains an agent that blocks the de novo synthesis of nucleotides. Exemplary and preferred agents are aminopterin, methotrexate, and azaserine. Aminopterin and methotrexate block de novo synthesis of both purine and pyrimidine nucleotides, whereas azaserine blocks only de novo nucleotide purine synthesis. Where aminopterin or methotrexate is used, the media is supplemented with hypoxanthine and thymidine as a source of nucleotides (HAT medium) by salvage pathways. Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and therefore, they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which particular clones are selected. The selection of hybridomas is performed by culturing the cells in microtiter plates, followed by testing the individual clonal supernatants (after about two to three weeks) for antibody producers using ELISA IgG assays. Antibody positive hybridomas are screened further for MAbs with desired reactivity using antigen based assays. Such assays are normally sensitive, simple, and rapid, such as radioimmunoassays, enzyme immunoassays, dot immunobinding assays, and the like.

The selected hybridomas are then serially diluted and cloned into individual antibody-producing cell lines, clones of which are then propagated indefinitely to provide MAbs. The cell lines can be exploited for MAb production in two basic ways.

A sample of the hybridoma can be injected (often into the peritoneal cavity) into a histo-compatible animal of the type that was used to provide the somatic and myeloma cells for the original fusion (e.g., a syngenetic mouse). Optionally, the animals are primed with a hydrocarbon, especially oils such as pristane (tetramethylpentadecane) prior to injection. The injected animal develops tumors secreting the specific monoclonal antibody produced by the antibody producing hybridoma. The ascites fluid of the animal, and in some cases blood, can then be obtained to provide MAbs in high concentration.

The individual cell lines could also be cultured in vitro; where the MAbs are naturally secreted into the culture medium from which they can be readily obtained in high concentrations.

MAbs produced by either means may be further purified, if desired, using filtration, centrifugation and various chromatographic methods such as HPLC or affinity chromatography.

Monoclonal antibodies are preferred since the hybridoma cells which produce them can be kept in vitro indefinitely, and the assay can be more accurate due to the higher selectivity that can be achieved with a monoclonal antibody assay. The raising of monoclonal antibodies is well known. Means for preparing and characterizing antibodies are also well known in the art. (See, e.g., Antibodies: A Laboratory Manual, Cold Spring Harbor Laboratory, 1988, which is incorporated herein by reference.)

Whether a monoclonal or polyclonal antibody is employed in the practice of this invention, the steps involved in carrying out an assay consistent with the teachings of this invention are the same. Broadly speaking, the assay of this invention involves first constructing a standard curve involving known concentrations and amounts of reagents that subsequently can be used in assays where the concentration of the polypeptide associated with the magnesium binding defect is being determined in plasma or other body fluid samples. These techniques, while not previously practiced in connection with this specific polypeptide, are otherwise known in the art as having been practiced in the detection of other analytes.

However, in the context of this invention, an assay can be practiced as follows. One way to construct an assay is to use the radioimmunoassay ("RIA"). As is known in the art, the RIA is an analytic technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto i.e., the antibody-antigen complex. Finally, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percentages of bound tracer antigens are plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoadsorbent may also be similarly counted. Then, from the standard curve, the concentration of antigen in the original sample is determined.

The first step in a standard curve is to incubate a fixed amount of the tracer analyte with a reagent blank and with a series of dilutions of the antibody in constant volumes of buffer containing bovine serum albumin ("BSA"). At the end of the incubations each of the antibody-tracer analyte complexes formed are precipitated by the addition of constant amounts of polyethyleneglycol 4000. The level of radioactivity of each precipitate is determined with the use of a suitable gamma counter. These values, in descending order, are plotted on the ordinate (normal scale) of semilog paper against the dilutions of antibody, in descending order (highest to lowest), plotted on the abscissa (log scale).

From this plot is read the dilution of antibody which combines with 50 percent of the labeled analyte. This particular combination of concentrations of tracer analyte and antibody is used for the construction of the standard curve.

To construct the standard curve, a second incubation is carried out under the same conditions as before except that the above dilution of antibody and concentation of tracer analyte are introduced together into a series of incubation tubes containing increasing concentrations of the standard analyte. The processes of incubation, precipitation of the antibody-analyte complexes, and quantification of the radioactivities are carried out as before. This time, a plot on semilog paper of the levels of radioactivity in descending order on the ordinate against the concentrations of standard analyte in ascending order on the abscissa is prepared and constitutes in the standard curve.

To determine the quantity of the polypeptide in a test sample, a third incubation is carried out using the conditions used in constructing the standard curve except that the ascending concentrations of standard analyte are replaced by two or more suitable dilutions of a concentrate of plasma polypeptides prepared as indicated above. The concentrations of analyte added to the incubation tubes are read from the standard curve by noting the concentration of standard that corresponds to each level of radioactivity measured for the tubes containing the unknowns. Such procedures can, of course, be automated, as is known in the art.

From the standpoint of good practice the standard curve should be developed each time unknown samples are assayed.

Once the conditions for the standard curve have been fine-tuned or adjusted so that the curve includes the concentrations of analyte likely to be encountered in a specific biological fluid, e.g. blood plasma, the standards and reagents, together with appropriate instructions for use, can be packaged in a "kit" for commercial distribution.

The principles involved in the radioinmuunoassay system above can also be applied to a variety of immunoassay systems, preferably competitive binding assays, of varying degrees of sensitivity for the quantification of the polypeptides involved in the detection of the magnesium binding defect. In each case, the antibody can be monoclonal or polyclonal. It is bound to a support so that the antibody-analyte complexes can be readily separated from the incubation mixtures. The labels used for forming the tracer analyte determine the sensitivities of the systems and provide for colorimetric (least sensitive), radioactive, fluorometric and chemiluminescent (most sensitive) endpoints. Consequently, the conventional apparatuses used for the determination of each type of endpoint will be required.

There are many ways the antibody may be bound and the tracer analyte labeled. For example, the antibody can be bound in the following ways:

a) Antibody adsorbed on a polystyrene tube or surface (microtiter plate). Complexes are isolated by washing.

b) Antibody adsorbed on a polyvinyl tube or surface (microtiter plate). Complexes are isolated by washing.

c) Antibody adsorbed on 6 mm polystyrene spheres. Complexes are isolated by centrifugation and washing.

d) Antibody adsorbed on 6 mm polyvinyl spheres. Complexes are isolated by centrifugation and washing.

e) Antibody bound to 5 um microparticles of paramagnetic ferrous oxide. The surfaces of particles are derivitized with a substance that has a terminal amino group. The antibody is linked to the surface by the use of glutaraldehyde. Complexes are isolated by applying a magnetic field to hold the particles against the surface of the incubation tube, and then washing.

f) Antibody bound to 5 um microparticles of paramagnetic chromium dioxide. Binding of antibody to surface of particles and isolation of complexes accomplished as described in (e) above.

g) Antibody bound to sepharose (an insoluble complex carbohydrate) after the surface of the sepharose is modified by use of cyanogen bromide. Complexes are isolated by centrifugating and washing.

h) Antibody bound to agarose (an insoluble complex carbohydrate). Binding of antibody and isolation of complexes are accomplished as in (g) above.

i) Antibody derivitized with biotin by use of biocytin and glutaraldehyde. (Biotinyl-N-hydroxysuccimide ester, or biotinyl-p-nitrophenyl ester, or caproylamidobiotinyl-N-hydroxy-succimimide ester may also be used for biotinylation). Complexes are isolated by allowing complex to combine with the protein avidin which is bound to a solid support such as plastic spheres, paramagnetic particles, or insoluble carbohydrates by the methods indicated above.

In general, the detection of immunocomplex formation is well known in the art and may be achieved through the application of a number of tags besides the radioactive tag used in the RIA described above. These other methods are based upon the detection of fluorescent, biological, or enzymatic tags, for example. Some examples include the following:

1) Analyte conjugated with horseradish peroxidase using glutaraldehyde. Quantification is accomplished by: a) measuring intensity of color produced in the presence of hydrogen peroxide and o-phenylenediamine or preferrably 3,3',5,5'-tetramethylbenzidine; b) measuring fluoresence intensity after the addition of hydrogen peroxide and fluorescein or rhodamine; c) by measuring chemiluminescence intensity after the addition of hydrogen peroxide and luminol plus benzothiazole. The equipment required includes calorimeter or spectrophotometer (unaided normal vision sufficient for qualitative assessment), spectrofluorimeter, or luminometer, respectively.

2) Analyte labeled with acridinium ester by use of 4-(2-succinimidyloxy-carbonyl ethyl)-phenyl-10-methylacridinium-9-carboxylate fluorosulfonate. Quantification is accomplished by measuring intensity of chemiluminescence produced by the addition of alkaline hydrogen peroxide. A luminometer is required.

3) Analyte labeled with fluorescein isothiocyanate. Quantification is accomplished by measuring the intensity of fluorescence after addition of hydrogen peroxide and a peroxidase such as horseradish peroxidase. A spectrofluorimeter is required.

4) Analyte labeled with alkaline phosphatase by use of glutaraldehyde. Quantification is accomplished by measuring intensity of fluorescence after addition of 4-methylumbelliferylphosphate. A spectrofluorimeter is obviously required.

5) Analyte labeled with rhodamine isothiocyanate. Quantification is accomplished the game as in (3) above.

6) Analyte labeled with glucose-6-phosphate dehydrogenase by use of glutaraldehyde. Quantification is accomplished by measuring ultraviolet light absorbed after the addition of glucose-6-phosphate and nicotinamide-adenine dinucleotide. A UV spectrophotometer is required.

7) Analyte labeled by conjugation with bacterial peroxidase. Conjugation and quantification is accomplished the same as in (1) above.

By use of one of the various bound forms of the antibody and of labeled forms of analyte described above it is possible to construct many kinds of competitive binding assay systems for the quantification of the pentapeptide (SEQ ID NO:1) and its tetrapeptide degradation product (SEQ ID NO:2) which occur in human blood plasma and prevent the occurrence of the magnesium binding defect in cell membranes. Alternatively, in each such system, the tracer analyte, rather than the antibody, can be the bound member of the system. Since these systems vary in their sensitivities and equipment requirements, it is possible to select a system according to the specific requirements of or adapted to the existing equipment employed by the user.

The specific reagents and other requirements for each system, except hardware, and directions for use can be packaged in "kits" containing various combinations of the above reagents, together with the necessary containers containing washing solutions, for commercial distribution.

While several embodiments of this invention have been described, others will readily be apparent to those skilled in the art. Such embodiments are included in this invention, unless the claims that follow expressly state otherwise.

I claim:

1. A method for detecting magnesium binding defect comprising:
   a) measuring in blood plasma the level of peptide having an amino acid sequence selected from the group consisting of: Phe-Phe-Gly-Leu-Met-$NH_2$ (SEQ ID NO:1), Phe-Xaa-Gly-Leu-Met-$NH_2$, where Xaa is variant Phe or Val (SEQ ID NO:4), and Phe-Gly-Leu-Met-$NH_2$ (SEQ ID NO:2);
   b) comparing said level to a standard, wherein a reduced level of said peptide is indicative of said magnesium binding defect.

2. The method of claim 1 wherein said level of peptide is measured by using an antibody to peptide having an amino acid sequence selected from the group consisting of: Phe-Phe-Gly-Leu-Met-$NH_2$ (SEQ ID NO:1), Phe-Xaa-Gly-Leu-Met-$NH_2$, where Xaa is variant Phe or Val (SEQ ID NO:4), and Phe-Gly-Leu-Met-$NH_2$ (SEQ ID NO:2).

3. The method of claim 2 wherein the antibody is monoclonal.

4. The method of claim 3 wherein the monoclonal antibody cross reacts with each of said peptides.

5. The method of claim 2 wherein the antibody is employed in an immunoenzyme assay.

6. The method of claim 5 wherein the immunoenzyme assay is enzyme-linked immunosorbent assay to quantitate the concentration of said peptide in blood plasma.

7. The method of claim 2 wherein the antibody is polyclonal.

* * * * *